(12) United States Patent
Ohrbom et al.

(10) Patent No.: US 7,087,675 B2
(45) Date of Patent: Aug. 8, 2006

(54) MONOMER AND POLYMERIZATION PROCESS

(75) Inventors: Walter H. Ohrbom, Hartland Township, MI (US); Patricia A. Herrel, Hartland Township, MI (US)

(73) Assignee: BASF Corporation, Southfield, MI (US)

( * ) Notice: Subject to any disclaimer, the term of this patent is extended or adjusted under 35 U.S.C. 154(b) by 306 days.

(21) Appl. No.: 10/391,839

(22) Filed: Mar. 19, 2003

(65) Prior Publication Data

US 2003/0166813 A1 Sep. 4, 2003

Related U.S. Application Data

(62) Division of application No. 09/316,591, filed on May 21, 1999, now Pat. No. 6,346,591.

(51) Int. Cl.
*C08J 3/00* (2006.01)

(52) U.S. Cl. ............... 524/590; 526/269; 526/310; 526/319; 526/320; 526/325; 526/321; 524/591; 524/598

(58) Field of Classification Search ............... 526/312, 526/269, 310, 319, 320, 321, 325; 524/590, 524/591, 598
See application file for complete search history.

(56) References Cited

U.S. PATENT DOCUMENTS

| | | | | |
|---|---|---|---|---|
| 2,806,838 A | * | 9/1957 | Melamed | 526/288 |
| 3,674,838 A | * | 7/1972 | Nordstrom | 560/166 |
| 4,126,747 A | * | 11/1978 | Cowherd et al. | 560/166 |
| 4,490,115 A | * | 12/1984 | Orlowski et al. | 433/199.1 |
| 5,292,833 A | * | 3/1994 | Grahe et al. | 525/531 |
| 5,478,870 A | * | 12/1995 | Kudoh et al. | 523/409 |
| 6,346,591 B1 | * | 2/2002 | Ohrbom et al. | 526/312 |
| 6,403,709 B1 | | 6/2002 | Ramesh et al. | 525/95 |
| 6,566,476 B1 | * | 5/2003 | Ohrbom et al. | 526/312 |
| 2002/0010254 A1 | | 1/2002 | Ramesh et al. | 524/501 |
| 2002/0132921 A1 | | 9/2002 | Ramesh et al. | 525/88 |
| 2003/0050424 A1 | | 3/2003 | Bernard | 528/49 |

FOREIGN PATENT DOCUMENTS

DE 19544671 A1 * 6/1997
WO WO-00/71505 A1 * 11/2000

OTHER PUBLICATIONS

Swaminathan Ramesh et al., U.S. Appl. No. 09/747,473, filed Dec. 22, 2000, entitled "Water-based Coating composition having carbamate-melamine cross-linking method of preparing the same, and a cured film thereof" pp. 1-39, and the abstract.

* cited by examiner

*Primary Examiner*—David W. Wu
*Assistant Examiner*—Henry S. Hu

(57) ABSTRACT

The β-hydroxy carbamate, ethylenically unsaturated monomer of the invention can be polymerized as a homopolymer or copolymerized with other monomers. The polymerization can be carried out in an aqueous medium. The β-hydroxy carbamate monomer is polymerized to form water-soluble homopolymers or, if polymerized as a mixture with one or more comonomers, copolymers that are soluble, emulsifiable, or dispersible in water. The β-hydroxy carbamate monomer can be used as a replacement monomer for acrylamide.

4 Claims, No Drawings

MONOMER AND POLYMERIZATION PROCESS

The present application is a divisional application of U.S. Ser. No. 09/316,591, filed May 21, 1999, now U.S. Pat. No. 6,346,591 which is incorporated herein by reference.

FIELD OF THE INVENTION

The invention concerns water-soluble and water-dispersible monomers and resins and processes for preparing aqueous resin compositions.

BACKGROUND OF THE INVENTION

Aqueous, resin compositions are widely used in many different fields, including coatings, inks, detergents, additives for plastics, water treatment, papermaking, and oil field production and refining. In particular, polyacrylamide and copolymers of acrylamide have gained prominence as non-ionic or cationic polymers that are water soluble. Because of industrial hygiene considerations associated with use of acrylamide monomer, a replacement for acrylamide has long been sought. Modifications such as N-substituted acrylamide monomers (e.g., N-methylol acrylamide) have been proposed. Polymers produced with the acrylamide and modified acrylamide monomers, however, have other shortcomings that make them undesirable. For example, the only reactive functional group of acrylamide is the unsaturation, so the polymerized acrylamide unit does not provide a site for crosslinking or further modification. Crosslinking or other modification of the acrylamide unit would be useful to reduce water sensitivity of the homopolymer or copolymer at an appropriate time.

Thus it would be desirable to provide a water soluble monomer that could be used in the place of acrylamide, would not have the industrial hygiene concerns associated with acrylamide, and could be modified when it would be appropriate to reduce the water sensitivity of a polymer prepared from the water soluble monomer.

SUMMARY OF THE INVENTION

We have now invented a method of preparing improved aqueous resin compositions. The resins are prepared by employing a β-hydroxy carbamate monomer. The β-hydroxy carbamate monomer is polymerized to form water-soluble homopolymers or, if polymerized as a mixture with one or more comonomers, copolymers that are soluble or dispersible in water. The β-hydroxy carbamate monomer of the invention can be used as a replacement for acrylamide, especially for preparing aqueous resin compositions. The β-hydroxy carbamate monomer offers an advantage of providing reactive sites for crosslinking or other reactions after polymerization.

When used in connection with the invention, the term "carbamate group" refers to a group having a structure

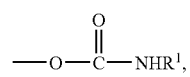

in which $R^1$ is H or alkyl. Preferably, $R^1$ is H or alkyl of from 1 to about 4 carbon atoms, and more preferably $R^1$ is H.

When polymerized, the monomer of the invention provides two reactive sites, a hydroxyl group and a reactive carbamate group, for crosslinking or other modification of the polymer.

DETAILED DESCRIPTION OF THE INVENTION

The β-hydroxy carbamate monomer has an ethylenically unsaturated group and a β-hydroxy carbamate group. Preferably, there are from 1 to about 4 carbons between the ethylenically unsaturated group and the β-hydroxy carbamate group. The β-hydroxy carbamate monomer of the invention can be represented by a structure:

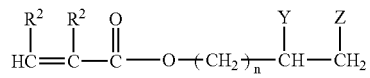

wherein either each $R^2$ is hydrogen or one $R^2$ is hydrogen and the other $R^2$ is methyl; n is from 1 to about 4, preferably 1; and one of Y and Z is OH and the other of Y and Z is

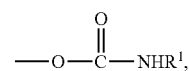

wherein $R^1$ is H or alkyl. Preferably, $R^1$ is H or alkyl of from 1 to about 4 carbon atoms, and more preferably $R^1$ is H. In a typical synthesis of the β-hydroxy carbamate monomer, the reaction kinetics produces a product that is a mixture of the compound in which Y is hydroxyl and Z is the carbamate group and the compound in which Z is a hydroxyl and Y is the carbamate group.

Unlike acrylonitrile, the monomer of the present invention has reaction rates comparable to other acrylic monomers. The monomer can be polymerized to form a homopolymer. The polymerization can be carried out in water or in an a mixture that includes water. The monomer of the invention can also be copolymerized with other monomers, including acrylic, methacrylic, vinylic and allylic monomers, again preferably in an aqueous medium. Particular examples of suitable comonomers include, without limitation, acrylic acid, methacrylic acid, crotonic acid, esters of these acids, maleic anhydride, styrene, alpha-methylstyrene, vinyl acetate, and so on. Other functional monomers may be copolymerized along with the β-hydroxy carbamate monomer, including, without limitation, acid- and anhydride-functional monomers such as those already mentioned; hydroxyl-functional monomers such as hydroxyalkyl acrylates and methacrylates, amino-functional acrylic monomers such as t-butylaminoethyl methacrylate and t-butylaminoethyl acrylate; epoxide-functional monomers such as glycidyl acrylate, glycidyl methacrylate, and allyl glycidyl ether; other carbamate-functional monomers, and so on.

One way of preparing the β-hydroxy carbamate monomer of the invention is by reacting a glycidyl-group containing polymerizable monomer first with carbon dioxide to convert the oxirane group to a cyclic carbonate group, and then with ammonia or a primary amine to convert the cyclic carbonate group to a β-hydroxy carbamate group. Examples of suitable oxirane group-containing polymerizable monomers include, without limitation, glycidyl acrylate, glycidyl methacrylate, glycidyl crotonate, and allyl glycidyl ether. Oxirane groups can be converted to carbamate groups by first converting to a cyclic carbonate group by reaction with $CO_2$. This can be done at any pressure from atmospheric up to supercritical $CO_2$ pressures, but is preferably under elevated pressure (e.g., 60–150 psi). The temperature for this reaction is preferably 60–150° C. Useful catalysts include any that activate an oxirane ring, such as tertiary amine or quaternary salts (e.g., tetramethyl ammonium bromide), combinations of complex organotin halides and alkyl phosphonium halides (e.g., $(CH_3)_3SnI$, $Bu_4SnI$, $Bu_4PI$, and $(CH_3)_4PI$), potassium salts (e.g., $K_2CO_3$, KI) preferably in combination with crown ethers, tin octoate, calcium octoate, and the like.

The cyclic carbonate group is reacted with ammonia or a primary amine. The primary amine preferably has up to four carbons, e.g. methyl amine. Preferably, the cyclic carbonate is reacted with ammonia. The ammonia may be aqueous ammonia (i.e., $NH_4OH$). The reaction ring-opens the cyclic carbonate to form a β-hydroxy carbamate monomer according to the invention.

The β-hydroxy carbamate monomer is water soluble. In one embodiment of the invention, the β-hydroxy carbamate monomer is polymerized to form a homopolymer. The homopolymer is water-soluble. The β-hydroxy carbamate monomer may be polymerized in the presence of free-radical initiators or with a redox initiator system. Useful initiators and redox initiator systems are well-known. The polymerization may be carried out without solvent or in an organic or aqueous medium. In a preferred embodiment, the β-hydroxy carbamate monomer is polymerized in an aqueous medium, preferably without any organic solvent or with a minor amount (up to about 10% by weight of the aqueous medium) of a polar solvent such as methanol, tetrahydrofuran, propylene glycol monomethyl ether, or other water-soluble or water-miscible solvents. The β-hydroxy carbamate monomer may be dissolved in water along with the initiating system and polymerized at a suitable temperature for the initiating system.

Alternatively, the β-hydroxy carbamate monomer may be polymerized as a mixture with one or more comonomers. Depending on the comonomers chosen, and the ratio of the β-hydroxy carbamate monomer with the other comonomers, the copolymers may be water soluble or water dispersible. As used herein, "dispersible" or "water dispersible" encompasses not only dispersible (solid) copolymers, but also emulsifiable or water emulsifiable copolymers, that is, copolymers that are liquids or above their $T_g$ at room temperatures and thus form emulsions. Examples of suitable comonomers include, without limitation, α,β-ethylenically unsaturated monocarboxylic acids containing 3 to 5 carbon atoms such as acrylic, methacrylic, and crotonic acids and the esters of those acids; α,β- unsaturated dicarboxylic acids containing 4 to 6 carbon atoms and the anhydrides, monoesters, and diesters of those acids; vinyl esters, vinyl ethers, vinyl ketones, and aromatic or heterocyclic aliphatic vinyl compounds. Representative examples of suitable esters of acrylic, methacrylic, and crotonic acids include, without limitation, those esters from reaction with saturated aliphatic and cycloaliphatic alcohols containing 1 to 20 carbon atoms, such as methyl, ethyl, propyl, isopropyl, n-butyl, isobutyl, tert-butyl, 2-ethylhexyl, lauryl, stearyl, cyclohexyl, trimethylcyclohexyl, tetrahydrofurfuryl, stearyl, sulfoethyl, and isobornyl acrylates, methacrylates, and crotonates; and polyalkylene glycol acrylates and methacrylates. Representative examples of other ethylenically unsaturated polymerizable monomers include, without limitation, such compounds as fumaric, maleic, and itaconic anhydrides, monoesters, and diesters with alcohols such as methanol, ethanol, propanol, isopropanol, butanol, isobutanol, and tert-butanol. Representative examples of polymerization vinyl monomers include, without limitation, such compounds as vinyl acetate, vinyl propionate, vinyl ethers such as vinyl ethyl ether, vinyl and vinylidene halides, and vinyl ethyl ketone. Representative examples of aromatic or heterocyclic aliphatic vinyl compounds include, without limitation, such compounds as styrene, α-methyl-styrene, vinyl toluene, tert-butyl styrene, and 2-vinyl pyrrolidone. The comonomers may be used in any combination.

Aqueous solutions including the β-hydroxy carbamate monomer may be polymerized in the presence of a free radical initiator at moderate temperatures, for example at temperature between about 20 and about 90° C. When a copolymer is emulsion polymerized, the β-hydroxy carbamate monomer is preferably used in an amount sufficient to stabilize the monomer emulsion during the polymerization process. Typically, the monomers may include from about 2 to 100 percent by weight, preferably from about 5 to 100 percent by weight, and more preferably from about 20 to 100 percent by weight, of the β-hydroxy carbamate monomer.

Suitable free radical initiators include, without limitation, peroxide, persulfates, redox couples, azo compounds, and nonchemical means including ultrasound, UV light, ionizing radiation, and so on. Chain transfer agents may be included. Specific examples of useful initiators include, without limitation, hydrogen peroxide, ammonium persulfate, and redox systems, for example the combination of reducing species such as $SO_3^-$ with oxidants such as $Fe^{+3}$ or the oxidation of thiourea by oxidants such as $Fe^{+3}$. Specific examples of chain transfer agents include isopropanol, thiols such as octanethiol or mercaptoethanol, organohalides such as chloroform, diacetone alcohol, and the dimer of α-methyl styrene.

The β-hydroxy carbamate monomer can also be polymerized by other methods suitable for ethylenically unsaturated monomers. For example, without limitation, the β-hydroxy carbamate monomer can be polymerized in an organic solvent, particularly a water miscible solvent. The homopolymer or copolymer of the β-hydroxy carbamate monomer may then be diluted with water or inverted into water with or without distillation or stripping of the organic solvent. Methods for inversion of a water-soluble or water-dispersible polymer from an organic medium into an aqueous medium are known.

In an alternative embodiment, the homopolymer or copolymer including β-hydroxy carbamate units may be prepared by including the corresponding cyclic carbonate monomer and forming the carbamate group from the carbonate group at some time during the polymerization of the corresponding cyclic carbonate monomer. For example, a primary amine or ammonia can be charged to the polymerization reactor and react with the cyclic carbonate group during the polymerization. The reactor can be pressurized for ammonia or a gaseous primary amine. The ammonia or primary amine could also be added during the polymerization reaction.

The homopolymers and copolymers of the β-hydroxy carbamate monomer may have weight average molecular weights of from about 5000 to over a million. The most desirable weight average molecular weight will depend upon the use intended for the polymer. When the β-hydroxy carbamate monomer is used as a replacement for acrylamide for a particular application, the amount of the β-hydroxy carbamate monomer included and the preferred weight average molecular weight of the polymer prepared from it is comparable to the corresponding values for an acrylamide polymer for that application.

Homopolymers and copolymers of the β-hydroxy carbamate monomer may be used in coating compositions, particularly waterborne coating compositions including topcoats. The homopolymers and copolymers of the β-hydroxy carbamate monomer may also be used in other applications, especially in applications where acrylamide polymers have been used, including, without limitation, leather treatment, textile treatments, crop protection uses such as seed coatings, and in manufacture of fibers and inks. A homopolymer of the β-hydroxy carbamate monomer may also be used as a dispersant or emulsifier for another polymer in preparing an aqueous composition. In particular, homopolymers or copolymers of the β-hydroxy carbamate monomer may be used to incorporate hydrophobic resins and polymers into aqueous compositions. For example, the β-hydroxy carbamate monomer may be used in the methods disclosed in Grandhee, U.S. Pat. Nos. 5,569,715 and 5,786,420 and Martin et al., U.S. Pat. No. 5,071,904, all three patents being incorporated herein by reference.

In one embodiment of the invention, the β-hydroxy carbamate monomer is copolymerized with at least one monomer capable of forming a cationic group in water when salted. Examples of such cation-forming monomers include those having an aromatic group, preferably a quaternary ammonium salt obtained by the reaction of benzyl chloride and with an amino monomer such as dimethylaminoethyl (meth)acrylate, diethylaminoethyl(meth)acrylate, and dimethylaminohydroxylpropyl (meth)acrylate. The cationic copolymer is useful in water treatment, papermaking, oil field production and refining applications.

In another preferred embodiment, the homopolymers and copolymers of the β-hydroxy carbamate monomer is used to prepare a coating composition. The coating composition preferably further includes a curing agent or crosslinker that is reactive with the one or both of the hydroxyl and carbamate functionalities of the β-hydroxy carbamate monomer. The curing agent has, on average, at least about two reactive functional groups. The functional groups may be of more than one kind, each kind being reactive with one or both of the hydroxyl and carbamate groups.

Useful curing agents include materials having active methylol or methylalkoxy groups, such as aminoplast crosslinking agents or phenol/formaldehyde adducts; curing agents that have isocyanate groups, particularly blocked isocyanate curing agents, curing agents that have epoxide groups, amine groups, acid groups, siloxane groups, cyclic carbonate groups, and anhydride groups; and mixtures thereof. Examples of preferred curing agent compounds include, without limitation, melamine formaldehyde resin (including monomeric or polymeric melamine resin and partially or fully alkylated melamine resin), blocked or unblocked polyisocyanates (e.g., toluene diisocyanate, MDI, isophorone diisocyanate, hexamethylene diisocyanate, biurets, allophanates, and isocyanurates of these, which may be blocked for example with, e.g., alcohols, pyrazole compounds, or oximes), urea resins (e.g., methylol ureas such as urea formaldehyde resin, alkoxy ureas such as butylated urea formaldehyde resin), polyanhydrides (e.g., polysuccinic anhydride), and polysiloxanes (e.g., trimethoxy siloxane). Another suitable crosslinking agent is tris(alkoxy carhonylamino) triazine (available from Cytec Industries under the tradename TACT). The curing agent may be combinations of these, particularly combinations that include aminoplast crosslinking agents. Aminoplast resins such as melamine formaldehyde resins or urea formaldehyde resins are especially preferred. Combinations of tris(alkoxy carbonylamino) triazine with a melamine formaldehyde resin and/or a blocked isocyanate curing agent are likewise suitable and desirable. Component (b) may also contain groups that are reactive with the carbamate group of component (a), such as an acrylic polymer containing polymerized isobutoxymethyl acrylamide groups.

When monomers having a reactive group other than carbamate or hydroxyl are included in the copolymer, a crosslinker suitable for that reactive group may be included in the composition.

Although aqueous coating compositions that are free of regulated volatile organic compounds are preferred, a solvent may optionally be utilized in the coating composition used in the practice of the present invention. In general, the solvent can be any organic solvent and/or water. In one preferred embodiment, the solvent is a polar organic solvent. More preferably, the solvent is selected from polar aliphatic solvents or polar aromatic solvents. Still more preferably, the solvent is a ketone, ester, acetate, aprotic amide, aprotic sulfoxide, aprotic amine, or a combination of any of these. Examples of useful solvents include, without limitation, methyl ethyl ketone, methyl isobutyl ketone, m-amyl acetate, ethylene glycol butyl ether acetate, propylene glycol monomethyl ether acetate, xylene, N-methylpyrrolidone, blends of aromatic hydrocarbons, and mixtures of these. In another preferred embodiment, the solvent is water or a mixture of water with small amounts of co-solvents.

The coating composition used in the practice of the invention may include a catalyst to enhance the cure reaction. For example, when aminoplast compounds, especially monomeric melamines, are used as a curing agent, a strong acid catalyst may be utilized to enhance the cure reaction. Such catalysts are well-known in the art and include, without limitation, p-toluene sulfonic acid, dinonylnaphthalene disulfonic acid, dodecylbenzenesulfonic acid, phenyl acid phosphate, monobutyl maleate, butyl phosphate, and hydroxy phosphate ester. Strong acid catalysts are often blocked, e.g. with an amine. Other catalysts that may be useful in the composition of the invention include Lewis acids, zinc salts, and tin salts.

In a preferred embodiment of the invention, the organic solvent is present in the coating composition in an amount of from 0 weight percent to about 99 weight percent, preferably from 0 weight percent to about 70 weight percent, and more preferably from about 1 weight percent to about 20 weight percent. In a more preferred embodiment, the coating composition is aqueous and includes water in an amount of from about 0.01 weight percent to about 99 weight percent, preferably from about 5 weight percent to about 80 weight percent, and more preferably from about 20 weight percent to about 70 weight percent.

Coating compositions can be coated on the article by any of a number of techniques well-known in the art. These include, for example, spray coating, dip coating, roll coating, curtain coating, and the like. For automotive body panels, spray coating is preferred.

The coating compositions of the invention include electrocoat primer compositions, primer surfacer compositions, and topcoat compositions, including one-layer pigmented topcoat compositions as well as either or both of the clearcoat and basecoat layers of a two-layer topcoat compositions. When the resins of the invention are utilized in aqueous compositions, they may include monomers with groups that can be salted, i.e., acid groups or amine groups.

In the case of electrocoat primer compositions, an acid group or amine group is used to deposit the resin on the anode or cathode.

Additional agents, for example surfactants, fillers, stabilizers, wetting agents, dispersing agents, adhesion promoters, UV absorbers, hindered amine light stabilizers, etc. may be incorporated into the coating composition. While such additives are well-known in the prior art, the amount used must be controlled to avoid adversely affecting the coating characteristics.

The coating composition according to the invention is preferably utilized in a high-gloss coating and/or as the clearcoat of a composite color-plus-clear coating. High-gloss coatings as used herein are coatings having a 20° gloss (ASTM D523-89) or a DOI (ASTM E430-91) of at least 80.

When the coating composition of the invention is used as a high-gloss pigmented paint coating or as a basecoat of a basecoat-clearcoat composite coating, the pigment may be any organic or inorganic compounds or colored materials, fillers, metallic or other inorganic flake materials such as mica or aluminum flake, and other materials of kind that the art normally includes in such coatings. Pigments and other insoluble particulate compounds such as fillers are usually used in the composition in an amount of 1% to 100%, based on the total solid weight of binder components (i.e., a pigment-to-binder ratio of 0.1 to 1).

When the coating composition according to the invention is used as the clearcoat or basecoat of a basecoat-clearcoat composite coating, the composition forming the other layer of the composite coating may any of a number of types well-known in the art, and does not require explanation in detail herein. Polymers known in the art to be useful in clearcoat and basecoat compositions include acrylics, vinyls, polyurethanes, polycarbonates, polyesters, alkyds, and polysiloxanes. Preferred polymers include acrylics and polyurethanes. In one preferred embodiment of the invention, the basecoat composition also utilizes a carbamate-functional acrylic polymer. Basecoat polymers may be thermoplastic, but are preferably crosslinkable and comprise one or more type of crosslinkable functional groups. Such groups include, for example, hydroxy, isocyanate, amine, epoxy, acrylate, vinyl, silane, and acetoacetate groups. These groups may be masked or blocked in such a way so that they are unblocked and available for the crosslinking reaction under the desired curing conditions, generally elevated temperatures. Useful crosslinkable functional groups include hydroxy, epoxy, acid, anhydride, silane, and acetoacetate groups. Preferred crosslinkable functional groups include hydroxy functional groups and amino functional groups.

The coating compositions described herein are preferably subjected to conditions so as to cure the coating layers. Although various methods of curing may be used, heat-curing is preferred. Generally, heat curing is effected by exposing the coated article to elevated temperatures provided primarily by radiative heat sources. Curing temperatures will vary depending on the particular blocking groups used in the cross-linking agents, however they generally range between 90° C. and 180° C. The first compounds according to the present invention are preferably reactive even at relatively low cure temperatures. Thus, in a preferred embodiment, the cure temperature is preferably between 115° C. and 150° C., and more preferably at temperatures between 115° C. and 140° C. for a blocked acid catalyzed system. For an unblocked acid catalyzed system, the cure temperature is preferably between 80° C. and 100° C. The curing time will vary depending on the particular components used, and physical parameters such as the thickness of the layers, however, typical curing times range from 15 to 60 minutes, and preferably 15–25 minutes for blocked acid catalyzed systems and 10–20 minutes for unblocked acid catalyzed systems.

The invention is further described in the following example. The example is merely illustrative and does not in any way limit the scope of the invention as described and claimed. All parts are parts by weight unless otherwise noted.

EXAMPLE 1

Preparation of β-Hydroxy Carbamate Propyl Methacrylate

A methanolic solution of the cyclic carbonate of glycidyl methacrylate (available from Dow Corp., Midland, Mich.) was prepared by dissolving 1095.4 grams of the cyclic carbonate of glycidyl methacrylate in 1140 grams of methanol. The dissolved monomer was reacted with anhydrous ammonia, which was bubbled into the solution over a period of about 2.75 hr. The initial temperature was about 17° C., and the exotherm peaked at about 30° C. and was controlled by holding the reactor in a cooling bath. After the ammonia add was ended, the reactor was closed. The contents of the flask were stirred for an additional 5 hrs. When infrared analysis showed no remaining carbonate, 0.1 gram of MEHQ was added to stabilize the monomer and the methanol and unreacted ammonia are distilled under vacuum to yield a solid product having a slight pink color from the MEHQ.

The solid product (1147 g) is dissolved in 751.8 grams of water to yield a 60.4% nonvolatile solution.

EXAMPLE 2

Preparation of a Homopolymer of β-Hydroxy Carbamate Propyl Methacrylate

A reactor was charged with 193.4 grams of deionized water and heated to 80° F. under a nitrogen atmosphere. After the water had reached 80° C., a mixture of 306.2 grams of the solution of Example 1 and 11.2 grams of ammonium persulfate was added over a period of one hour. A solution of 0.9 grams of ammonium persulfate in 10 grams of deionized water was added over about 15 minutes. The reaction mixture was held for about 45 minutes longer, then cooled. The product was an aqueous polymer solution that had a faint haze.

EXAMPLE 3

Preparation of a Coating Composition Containing the Homopolymer of β-Hydroxy Carbamate Propyl Methacrylate A coating composition was prepared by combining 21.3 grams of the aqueous homopolymer solution of Example 2 with 6.1 grams of hexamethoxymethylated melamine and 0.2 gram of an acid catalyst (70% solution of dodecylbenzene sulfonic acid). The mixture was drawn down 7 mm thick over a steel panel primed with electrocoat primer. The drawn down coating layer was allowed to flash to 10 minutes at 180° F. to aid in evaporation of the water. The coating layer was baked for 30 minutes at 285° F. The resulting cured film was hard and passed solvent resistance tests of 200 double rubs with methyl ethyl ketone and a one-minute soak in methyl ethyl ketone.

The coating composition of Example 3 was examined for 7 mil drawdowns cured at 285° F. for 30 minutes on the substrates shown in the table below.

| | | |
|---|---|---|
| Parts of homopolymer (NV) | 12.9 | 12.9 |
| Parts of Resimene 747 (from Solutia) | 6.1 | 6.1 |
| Parts of dodecylbenzene sulfonic acid | 0.14 | 0.14 |
| Substrate | Electrocoat primed panel | Steel panel |
| 200 MEK double rubs | pass | pass |
| 1 minute MEK Soak | no effect | no effect |

EXAMPLE 4

Preparation of β-Hydroxy Carbamate Propyl Methacryate

A mixture of 200 parts by weight of the cyclic carbonate of glycidyl methacrylate in 50.7 parts by weight of deionized water was charged to a reaction vessel and 59.6 parts by weight of concentrated ammonium hydroxide (28 to 32% ammonia) were slowly added. The two phase system slowly converted into one phase as the carbonate monomer reacted to form the β-hydroxy carbamate propyl methacrylate product.

EXAMPLE 5

Preparation of Emulsion of a Copolymer of β-Hydroxy Carbamate Propyl Methacrylate The following materials were homogenized in two passes at 8000 PSI using a Microfluidizer® (Microfluidics Corporation) to form a homogenized monomer mixture using the techniques described in U.S. Pat. Nos. 5,786,420 and 5,569,715: 1062 parts by weight of a polyurethane polymer (80% NV by weight the reaction product of 1507 parts by weight of a polyester (theoretical OH equivalent weight of 748), 158 parts by weight of neopentyl glycol, 83 parts by weight of trimethylolpropane monoallyl ether, 1012 parts by weight of tetramethyl-m-xylene diisocyanate, and 288 parts by weight of trimethylolpropane), 747 parts by weight of methyl methacrylate, 356 parts by weight of butyl acrylate, 118 parts by weight of 2-hydroxyethyl methacrylate, 237 parts by weight of butyl methacrylate, 2010 parts by weight of deionized water, and 264 parts by weight of ABEX EP 110 (available from Rhodia Corp.).

In a suitable reactor, 360 parts by weight of deionized water was heated under an inert atmosphere to 82° C. A total of 756 parts by weight of the homogenized monomer mixture and a solution of 0.81 parts by weight of ammonium persulfate in 45 parts by weight of deionized water were added concurrently over 1.5 hours.

When both additions were complete, a mixture of 135 parts by weight of methyl methacrylate, 101 parts by weight of butyl acrylate, 75 parts by weight of the aqueous β-hydroxy carbamate propyl methacrylate solution of Example 4, 56 parts by weight of butyl methacrylate, 11.8 parts by weight of methacrylic acid, and 1.5 parts by weight of Igepal CO-850 (from Rhodia) was added over two hours. The reaction mixture was then held for two hours at 82° C. The final product had a measured nonvolatile by weight of 46.3% and a particle size of 215 nm.

EXAMPLE 6

Preparation of Emulsion of a Copolymer of β-Hydroxy Carbamate Propyl Methacrylate This example is similar to Example 5, but does not include the 2-hydroxyethyl methacrylate monomer in the polymerization.

The following materials were homogenized in two passes at 8000 PSI using a Microfluidizer® (Microfluidics Corporation) to form a homogenized monomer mixture using the techniques described in U.S. Pat. Nos. 5,786,420 and 5,569,715: 176 parts by weight of the polyurethane polymer described in Example 5, 86 parts by weight of methyl methacrylate, 64 parts by weight of butyl acrylate, 43 parts by weight of butyl methacrylate, 48 parts by weight of the aqueous β-hydroxy carbamate propyl methacrylate solution of Example 4, 364 parts by weight deionized water, and 48 parts by weight of ABEX EP 110.

In a suitable reactor, 365 parts by weight of deionized water was heated under an inert atmosphere to 82° C. A total of 770 parts by weight of the homogenized monomer mixture and a mixture of 44 parts by weight of deionized water and 0.81 parts by weight of ammonium persulfate were added concurrently over 1.5 hours.

When both additions were complete, a mixture of 145 parts by weight of methyl methacrylate, 100 parts by weight of butyl acrylate, 74 parts by weight of the aqueous β-hydroxy carbamate propyl methacrylate solution of Example 4, 55 parts by weight of butyl methacrylate, and 1.5 parts by weight of Igepal CO-850 (from Rhodia) was added over two hours. The reaction mixture was then held for two hours at 82° C. The final product had a measured nonvolatile by weight of 44% and a particle size of 181 nm.

Comparative Example A

The following materials were homogenized in two passes at 8000 PSI using a Microfluidizer® (Microfluidics Corporation) to form a homogenized monomer mixture using the techniques described in U.S. Pat. Nos. 5,786,420 and 5,569,715: 1062 parts by weight of the polyurethane polymer described in Example 5, 107 parts by weight of methyl methacrylate, 64 parts by weight of butyl acrylate, 43 parts by weight of butyl methacrylate, 363.1 parts by weight of deionized water, and 48 parts by weight of ABEX EP 110.

In a suitable reactor, 369 parts by weight of deionized water was heated under an inert atmosphere to 82° C. A total of 774 parts by weight of the homogenized monomer mixture and a solution of 0.83 parts by weight of ammonium persulfate in 46 parts by weight of deionized water were added concurrently over 1.5 hours.

When both additions were complete, a mixture of 173 parts by weight of methyl methacrylate, 104 parts by weight of butyl acrylate, 57 parts by weight of butyl methacrylate, and 1.5 parts by weight of Igepal CO-850 was added over two hours. The reaction mixture was then held for two hours at 82° C. The final product had a measured nonvolatile by weight of 45.4% and a particle size of 220 nm.

Curable Compositions

The emulsion copolymers of Example 5, Example 6, and Comparative Example A were formulated into thermosetting compositions and tested for curing properties. The cure profiles were established using 8 mil drawdowns on glass slides, and curing at 285° F. for 30 minutes. The systems were evaluated for cure using 200 double rubs with methyl ethyl ketone.

| Parts by weight Resin | Parts by weight Resimene 747[1] | Parts by weight dodecylbenzene sulfonic acid | Results of 200 MEK double rubs |
|---|---|---|---|
| 100 parts Example 5 | 1.28 | 0.09 | Pass |
| 100 parts Example 5 | 1.28 | 0.00 | Pass |
| 100 parts Example 5 | 0.00 | 0.00 | Failed |
| 100 parts Example 6 | 1.28 | 0.00 | Pass |
| 100 parts Comp. Ex. A | 1.28 | 0.00 | Failed |

[1] available from Solutia

The results in the above table demonstrate that the monomer of the invention provides groups available for crosslinking in thermosetting compositions.

The invention has been described in detail with reference to preferred embodiments thereof. It should be understood, however, that variations and modifications can be made within the spirit and scope of the invention and of the following claims.

What is claimed is:

1. A composition comprising water, a compound having a structure

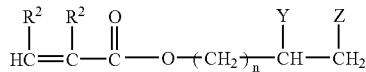

wherein either each $R^2$ is hydrogen or one $R^2$ is hydrogen and the other $R^2$ is methyl; n is from 1 to about 4; and one of Y and Z is OH and the other of Y and Z is

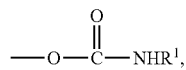

wherein $R^1$ is H or alkyl, and one or more further additional polymerizable monomers, wherein the compound is present in an amount sufficient to stabilize an emulsion of the further monomers in the water.

2. A composition according to claim 1, wherein $R^1$ is H.

3. A composition comprising water, a compound having a structure

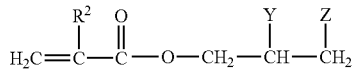

wherein $R^2$ is hydrogen or methyl and one of Y and Z is OH and the other of Y and Z is

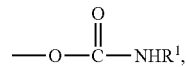

wherein $R^1$ is H or alkyl, and one or more further additional polymerizable monomers, wherein the compound is present in an amount sufficient to stabilize an emulsion of the further monomers in the water.

4. A method of preparing an aqueous composition, comprising a step of dispersing a hydrophobic polymer using a polymer having a structure

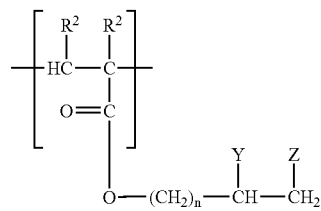

wherein either each $R^2$ is hydrogen or one $R^2$ is hydrogen and the other $R^2$ is methyl; n is from 1 to about 4; and one of Y and Z is OH and the other of Y and Z is

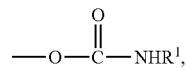

wherein $R^1$ is H or alkyl.

* * * * *